United States Patent
Arneson et al.

(10) Patent No.: US 8,647,259 B2
(45) Date of Patent: Feb. 11, 2014

(54) ULTRASOUND SCANNING CAPSULE ENDOSCOPE (USCE)

(75) Inventors: Michael Arneson, Finksburg, MD (US); William Bandy, Gambrills, MD (US); Wayne Shanks, Baltimore, MD (US)

(73) Assignee: Innurvation, Inc., Gambrills, MD (US)

( * ) Notice: Subject to any disclaimer, the term of this patent is extended or adjusted under 35 U.S.C. 154(b) by 0 days.

(21) Appl. No.: 13/073,424

(22) Filed: Mar. 28, 2011

(65) Prior Publication Data

US 2012/0101386 A1 Apr. 26, 2012

Related U.S. Application Data

(60) Provisional application No. 61/318,012, filed on Mar. 26, 2010.

(51) Int. Cl.
*A61B 1/04* (2006.01)
(52) U.S. Cl.
USPC ............ 600/109; 600/117; 600/437; 600/459
(58) Field of Classification Search
USPC ......... 600/437–469, 107–118, 160, 165–177, 600/593
See application file for complete search history.

(56) References Cited

U.S. PATENT DOCUMENTS

| | | |
|---|---|---|
| 2,788,390 A | 4/1957 | Sheldon |
| 2,987,960 A | 6/1961 | Sheldon |
| 3,329,074 A | 7/1967 | Gosselin |
| 3,608,547 A | 9/1971 | Sato et al. |
| 3,730,175 A | 5/1973 | Fukami et al. |
| 4,987,897 A | 1/1991 | Funke |
| 5,010,412 A | 4/1991 | Garriss |
| 5,131,398 A | 7/1992 | Alfano et al. |
| 5,251,326 A | 10/1993 | Silverman |
| 5,265,603 A | 11/1993 | Hudrlik |
| 5,267,033 A | 11/1993 | Hoshino |
| 5,279,607 A | 1/1994 | Schentag et al. |
| 5,329,498 A | 7/1994 | Greenstein |
| 5,395,366 A | 3/1995 | D'Andrea et al. |
| 5,522,865 A | 6/1996 | Schulman et al. |
| 5,559,757 A | 9/1996 | Catipovic et al. |
| 5,604,531 A | 2/1997 | Iddan et al. |
| 5,741,311 A | 4/1998 | McVenes et al. |
| 5,744,898 A | 4/1998 | Smith et al. |

(Continued)

FOREIGN PATENT DOCUMENTS

| | | |
|---|---|---|
| EP | 1 326 432 A2 | 7/2003 |
| EP | 1 492 352 A2 | 12/2004 |

(Continued)

*Primary Examiner* — Sanjay Cattungal
(74) *Attorney, Agent, or Firm* — Sterne, Kessler, Goldstein & Fox P.L.L.C.

(57) ABSTRACT

The present invention relates to ultrasound imaging on a capsule endoscope platform. It relates to the generation of a focused ultrasound acoustic signal and the receiving of echo signals from the wall of a body lumen with an array of acoustic transducers wrapped around the circumference of the capsule. It relates to sending the generated echo image signals to receiver devices attached or worn on the body. It relates to the generation of 360° overlapping sidewall ultrasound scans of a body lumen, and image processing techniques to assemble these scans into a high resolution continuous ultrasound image. Finally, it relates to the manufacture and assembly of such an ultrasound scanning capsule endoscope (USCE). The concept is extendable to conventional endoscopes and catheters.

22 Claims, 16 Drawing Sheets

(56) References Cited

U.S. PATENT DOCUMENTS

| | | | |
|---|---|---|---|
| 5,796,827 | A | 8/1998 | Coppersmith et al. |
| 5,833,603 | A | 11/1998 | Kovacs et al. |
| 5,984,875 | A | 11/1999 | Brune |
| 5,993,378 | A * | 11/1999 | Lemelson ..................... 600/109 |
| 5,995,136 | A | 11/1999 | Hattori et al. |
| 6,076,016 | A | 6/2000 | Feierbach |
| 6,104,913 | A | 8/2000 | McAllister |
| 6,115,636 | A | 9/2000 | Ryan |
| 6,172,789 | B1 | 1/2001 | Kino et al. |
| 6,198,965 | B1 | 3/2001 | Penner et al. |
| 6,211,799 | B1 | 4/2001 | Post et al. |
| 6,239,724 | B1 | 5/2001 | Doron et al. |
| 6,240,312 | B1 | 5/2001 | Alfano et al. |
| 6,294,775 | B1 | 9/2001 | Seibel et al. |
| 6,380,858 | B1 | 4/2002 | Yarin et al. |
| D457,236 | S | 5/2002 | Meron et al. |
| D457,621 | S | 5/2002 | Meron et al. |
| D457,948 | S | 5/2002 | Meron et al. |
| 6,431,175 | B1 | 8/2002 | Penner et al. |
| D464,425 | S | 10/2002 | Meron et al. |
| 6,486,588 | B2 | 11/2002 | Doron et al. |
| 6,504,286 | B1 | 1/2003 | Porat et al. |
| D469,864 | S | 2/2003 | Meron et al. |
| 6,563,105 | B2 | 5/2003 | Seibel et al. |
| 6,580,858 | B2 | 6/2003 | Chen et al. |
| 6,584,348 | B2 | 6/2003 | Glukhovsky |
| 6,597,320 | B2 | 7/2003 | Maeda et al. |
| 6,607,301 | B1 | 8/2003 | Glukhovsky et al. |
| 6,628,989 | B1 | 9/2003 | Penner et al. |
| 6,632,171 | B2 | 10/2003 | Iddan et al. |
| 6,702,755 | B1 | 3/2004 | Stasz et al. |
| 6,720,709 | B2 | 4/2004 | Porat et al. |
| D492,403 | S | 6/2004 | Iddan et al. |
| 6,754,472 | B1 | 6/2004 | Williams et al. |
| 6,764,446 | B2 | 7/2004 | Wolinsky et al. |
| 6,836,377 | B1 | 12/2004 | Kislev et al. |
| 6,845,190 | B1 | 1/2005 | Smithwick et al. |
| 6,847,844 | B2 | 1/2005 | Sun et al. |
| 6,855,111 | B2 | 2/2005 | Yokoi et al. |
| 6,856,712 | B2 | 2/2005 | Fauver et al. |
| 6,867,753 | B2 | 3/2005 | Chinthammit et al. |
| 6,904,308 | B2 | 6/2005 | Frisch et al. |
| 6,918,872 | B2 | 7/2005 | Yokoi et al. |
| 6,934,093 | B2 | 8/2005 | Kislev et al. |
| 6,934,573 | B1 | 8/2005 | Glukhovsky et al. |
| 6,936,003 | B2 | 8/2005 | Iddan |
| D510,139 | S | 9/2005 | Gilad et al. |
| 6,939,290 | B2 | 9/2005 | Iddan |
| 6,939,292 | B2 | 9/2005 | Mizuno |
| 6,944,316 | B2 | 9/2005 | Glukhovsky et al. |
| 6,950,690 | B1 | 9/2005 | Meron et al. |
| 6,958,034 | B2 | 10/2005 | Iddan |
| D512,150 | S | 11/2005 | Iddan et al. |
| 6,975,898 | B2 | 12/2005 | Seibel |
| 6,984,205 | B2 | 1/2006 | Gazdzinski |
| 6,986,738 | B2 | 1/2006 | Glukhovsky et al. |
| 7,009,634 | B2 | 3/2006 | Iddan et al. |
| 7,022,066 | B2 | 4/2006 | Yokoi et al. |
| 7,024,248 | B2 | 4/2006 | Penner et al. |
| 7,039,453 | B2 | 5/2006 | Mullick et al. |
| 7,060,094 | B2 * | 6/2006 | Shahinpoor et al. ........... 623/4.1 |
| 7,109,859 | B2 | 9/2006 | Peeters |
| 7,118,529 | B2 | 10/2006 | Glukhovsky et al. |
| 7,118,531 | B2 | 10/2006 | Krill |
| 7,119,814 | B2 | 10/2006 | Meron et al. |
| 7,122,001 | B2 | 10/2006 | Uchiyama et al. |
| 7,140,766 | B2 | 11/2006 | Glukhovsky et al. |
| 7,160,258 | B2 | 1/2007 | Imran et al. |
| 7,161,164 | B2 | 1/2007 | Glukhovsky |
| 7,195,588 | B2 | 3/2007 | Homan et al. |
| 7,200,253 | B2 | 4/2007 | Glukhovsky et al. |
| D543,272 | S | 5/2007 | Gilad et al. |
| 7,251,383 | B2 | 7/2007 | Iddan |
| 7,295,226 | B1 | 11/2007 | Meron et al. |
| 7,307,544 | B2 | 12/2007 | Kim et al. |
| 7,316,647 | B2 | 1/2008 | Kimoto et al. |
| 7,319,896 | B2 | 1/2008 | Konno |
| 7,327,525 | B2 | 2/2008 | Kislev et al. |
| 7,336,833 | B2 | 2/2008 | Horn |
| 7,343,036 | B2 | 3/2008 | Kleen et al. |
| 7,347,817 | B2 | 3/2008 | Glukhovsky et al. |
| 7,348,571 | B2 | 3/2008 | Ue |
| 7,354,397 | B2 | 4/2008 | Fujita et al. |
| 7,452,338 | B2 * | 11/2008 | Taniguchi ..................... 600/593 |
| 7,488,287 | B2 * | 2/2009 | Kawashima ................. 600/443 |
| 7,511,733 | B2 * | 3/2009 | Takizawa et al. ............... 348/68 |
| 7,647,090 | B1 | 1/2010 | Frisch et al. |
| 7,664,174 | B2 | 2/2010 | Avni et al. |
| 7,775,977 | B2 * | 8/2010 | Kawashima et al. ......... 600/437 |
| 7,805,178 | B1 | 9/2010 | Gat |
| 7,833,151 | B2 | 11/2010 | Khait et al. |
| 7,841,981 | B2 * | 11/2010 | Kawano et al. ............... 600/118 |
| 7,866,322 | B2 | 1/2011 | Iddan |
| 7,872,667 | B2 | 1/2011 | Iddan et al. |
| 7,931,584 | B2 * | 4/2011 | Akagi et al. .................. 600/101 |
| 7,940,603 | B2 * | 5/2011 | Adachi et al. ................. 367/181 |
| 7,998,067 | B2 * | 8/2011 | Kimoto et al. ................ 600/173 |
| 8,026,651 | B2 * | 9/2011 | Wakabayashi et al. ........ 310/344 |
| 8,036,731 | B2 | 10/2011 | Kimchy et al. |
| 8,047,995 | B2 * | 11/2011 | Wakabayashi et al. ........ 600/459 |
| 8,118,774 | B2 * | 2/2012 | Dann et al. .................. 604/95.04 |
| 8,125,516 | B2 | 2/2012 | Iddan et al. |
| 2001/0035902 | A1 | 11/2001 | Iddan et al. |
| 2002/0032366 | A1 | 3/2002 | Iddan et al. |
| 2002/0109774 | A1 | 8/2002 | Meron et al. |
| 2002/0138009 | A1 | 9/2002 | Brockway et al. |
| 2002/0158976 | A1 | 10/2002 | Vni et al. |
| 2002/0165592 | A1 | 11/2002 | Glukhovsky et al. |
| 2002/0168144 | A1 | 11/2002 | Chen et al. |
| 2002/0173718 | A1 | 11/2002 | Frisch et al. |
| 2002/0177779 | A1 | 11/2002 | Adler et al. |
| 2002/0193669 | A1 | 12/2002 | Glukhovsky |
| 2002/0198470 | A1 | 12/2002 | Imran |
| 2003/0013370 | A1 | 1/2003 | Glukhovsky |
| 2003/0018280 | A1 | 1/2003 | Lewkowicz et al. |
| 2003/0020810 | A1 * | 1/2003 | Takizawa et al. ............... 348/68 |
| 2003/0028078 | A1 | 2/2003 | Glukhovsky |
| 2003/0040685 | A1 | 2/2003 | Lewkowicz et al. |
| 2003/0043263 | A1 | 3/2003 | Glukhovsky et al. |
| 2003/0045790 | A1 | 3/2003 | Lewkowicz et al. |
| 2003/0077223 | A1 | 4/2003 | Glukhovsky et al. |
| 2003/0114742 | A1 | 6/2003 | Lewkowicz et al. |
| 2003/0117491 | A1 | 6/2003 | Avni et al. |
| 2003/0139647 | A1 | 7/2003 | Raz et al. |
| 2003/0139661 | A1 | 7/2003 | Kimchy et al. |
| 2003/0174208 | A1 | 9/2003 | Glukhovsky et al. |
| 2003/0195415 | A1 | 10/2003 | Iddan |
| 2004/0027500 | A1 | 2/2004 | Davidson et al. |
| 2004/0032187 | A1 | 2/2004 | Penner et al. |
| 2004/0073087 | A1 | 4/2004 | Glukhovsky et al. |
| 2004/0109488 | A1 | 6/2004 | Glukhovsky et al. |
| 2004/0114856 | A1 | 6/2004 | Kubby et al. |
| 2004/0122315 | A1 | 6/2004 | Krill |
| 2004/0127785 | A1 | 7/2004 | Davidson et al. |
| 2004/0138532 | A1 | 7/2004 | Glukhovsky |
| 2004/0171915 | A1 | 9/2004 | Glukhovsky et al. |
| 2004/0176685 | A1 * | 9/2004 | Takizawa et al. ............. 600/424 |
| 2004/0181155 | A1 | 9/2004 | Glukhovsky |
| 2004/0199054 | A1 | 10/2004 | Wakefield |
| 2004/0199061 | A1 | 10/2004 | Glukhovsky |
| 2004/0199222 | A1 | 10/2004 | Sun et al. |
| 2004/0202339 | A1 | 10/2004 | O'Brien, Jr. et al. |
| 2004/0204744 | A1 | 10/2004 | Penner et al. |
| 2004/0210105 | A1 | 10/2004 | Hale et al. |
| 2004/0236182 | A1 | 11/2004 | Iddan et al. |
| 2004/0240077 | A1 | 12/2004 | Kislev et al. |
| 2004/0258328 | A1 | 12/2004 | Adler |
| 2005/0025368 | A1 | 2/2005 | Glukhovsky |
| 2005/0065441 | A1 | 3/2005 | Glukhovsky |
| 2005/0068416 | A1 | 3/2005 | Glukhovsky et al. |
| 2005/0075555 | A1 | 4/2005 | Glukhovsky et al. |
| 2005/0088299 | A1 | 4/2005 | Bandy et al. |
| 2005/0096526 | A1 * | 5/2005 | Reinschke ..................... 600/407 |
| 2005/0110881 | A1 | 5/2005 | Glukhovsky et al. |

(56) References Cited

U.S. PATENT DOCUMENTS

| | | | |
|---|---|---|---|
| 2005/0119577 A1* | 6/2005 | Taniguchi | 600/459 |
| 2005/0143644 A1 | 6/2005 | Gilad et al. | |
| 2005/0148816 A1 | 7/2005 | Glukhovsky et al. | |
| 2005/0159643 A1 | 7/2005 | Zinaty et al. | |
| 2005/0159789 A1 | 7/2005 | Brockway et al. | |
| 2005/0171398 A1 | 8/2005 | Khait et al. | |
| 2005/0177026 A1 | 8/2005 | Hoeg et al. | |
| 2005/0185299 A1 | 8/2005 | Kislev et al. | |
| 2005/0187433 A1 | 8/2005 | Horn et al. | |
| 2005/0203417 A1* | 9/2005 | Okuno | 600/463 |
| 2005/0222490 A1 | 10/2005 | Glukhovsky et al. | |
| 2005/0228259 A1 | 10/2005 | Glukhovsky et al. | |
| 2005/0228275 A1* | 10/2005 | Kawashima | 600/437 |
| 2005/0266074 A1 | 12/2005 | Zilberstein et al. | |
| 2005/0272974 A1 | 12/2005 | Iddan | |
| 2005/0279799 A1* | 12/2005 | Kubokawa et al. | 224/665 |
| 2005/0281446 A1 | 12/2005 | Glukhovsky et al. | |
| 2006/0004256 A1 | 1/2006 | Gilad et al. | |
| 2006/0009818 A1 | 1/2006 | Von Arx et al. | |
| 2006/0036131 A1 | 2/2006 | Glukhovsky et al. | |
| 2006/0045118 A1 | 3/2006 | Hyoung et al. | |
| 2006/0074275 A1 | 4/2006 | Davidson et al. | |
| 2006/0082648 A1 | 4/2006 | Iddan et al. | |
| 2006/0092908 A1 | 5/2006 | Sung et al. | |
| 2006/0116584 A1 | 6/2006 | Sudol et al. | |
| 2006/0122461 A1 | 6/2006 | Kislev et al. | |
| 2006/0132599 A1 | 6/2006 | Iddan et al. | |
| 2006/0147037 A1 | 7/2006 | Boschetti | |
| 2006/0149132 A1 | 7/2006 | Iddan | |
| 2006/0155174 A1 | 7/2006 | Glukhovsky et al. | |
| 2006/0158512 A1 | 7/2006 | Iddan et al. | |
| 2006/0184039 A1 | 8/2006 | Avni et al. | |
| 2006/0192889 A1 | 8/2006 | Iddan et al. | |
| 2006/0232668 A1 | 10/2006 | Horn et al. | |
| 2006/0238879 A1 | 10/2006 | Togino | |
| 2006/0252371 A1 | 11/2006 | Yanagida | |
| 2006/0252986 A1* | 11/2006 | Akagi et al. | 600/101 |
| 2007/0002135 A1 | 1/2007 | Glukhovsky | |
| 2007/0002604 A1 | 1/2007 | Lin et al. | |
| 2007/0043310 A1 | 2/2007 | Trandafir et al. | |
| 2007/0060798 A1 | 3/2007 | Krupnik et al. | |
| 2007/0060979 A1 | 3/2007 | Strother et al. | |
| 2007/0078335 A1 | 4/2007 | Horn | |
| 2007/0123772 A1 | 5/2007 | Euliano et al. | |
| 2007/0185381 A1* | 8/2007 | Kimoto et al. | 600/117 |
| 2007/0213659 A1 | 9/2007 | Trovato et al. | |
| 2007/0221233 A1* | 9/2007 | Kawano et al. | 128/899 |
| 2007/0232874 A1 | 10/2007 | Ince | |
| 2007/0264732 A1* | 11/2007 | Chen | 438/22 |
| 2007/0265496 A1* | 11/2007 | Kawano et al. | 600/109 |
| 2007/0282156 A1 | 12/2007 | Konings | |
| 2008/0015411 A1* | 1/2008 | Kimoto et al. | 600/109 |
| 2008/0058597 A1 | 3/2008 | Arneson et al. | |
| 2008/0146871 A1 | 6/2008 | Arneson et al. | |
| 2008/0213355 A1 | 9/2008 | Bohmer | |
| 2009/0088618 A1 | 4/2009 | Arneson et al. | |
| 2009/0253999 A1* | 10/2009 | Aoki et al. | 600/565 |
| 2010/0130822 A1* | 5/2010 | Katayama et al. | 600/118 |
| 2010/0179381 A1* | 7/2010 | Kawano et al. | 600/104 |
| 2010/0217079 A1* | 8/2010 | Tichy | 600/118 |
| 2010/0251823 A1* | 10/2010 | Adachi et al. | 73/606 |
| 2010/0268058 A1* | 10/2010 | Chen | 600/407 |
| 2011/0060189 A1* | 3/2011 | Belson | 600/117 |

FOREIGN PATENT DOCUMENTS

| | | |
|---|---|---|
| EP | 1 637 917 A1 | 3/2006 |
| EP | 1 654 983 A1 | 5/2006 |
| EP | 1676522 | 7/2006 |
| EP | 1 693 000 A2 | 8/2006 |
| EP | 1 698 278 A1 | 9/2006 |
| EP | 1 704 812 A1 | 9/2006 |
| EP | 1 707 105 A1 | 10/2006 |
| EP | 1 715 697 A2 | 10/2006 |
| EP | 1 737 124 A2 | 12/2006 |
| GB | 2 414 408 A | 11/2005 |
| WO | WO 02/054932 A2 | 7/2002 |
| WO | WO 02/055126 A2 | 7/2002 |
| WO | WO 02/055984 A2 | 7/2002 |
| WO | WO 02/073507 A2 | 9/2002 |
| WO | WO 02/080376 A2 | 10/2002 |
| WO | WO 02/080753 A2 | 10/2002 |
| WO | WO 02/089913 A2 | 11/2002 |
| WO | WO 02/094337 A2 | 11/2002 |
| WO | WO 03/003706 A2 | 1/2003 |
| WO | WO 03/010967 A1 | 2/2003 |
| WO | WO 03/028224 A2 | 4/2003 |
| WO | WO 03/053241 A2 | 7/2003 |
| WO | WO 2004/014227 A1 | 2/2004 |
| WO | WO 2004/052209 A1 | 6/2004 |
| WO | WO 2004/054430 A2 | 7/2004 |
| WO | WO 2004/058041 A2 | 7/2004 |
| WO | WO 2004/096008 A2 | 11/2004 |
| WO | WO 2005/062715 A2 | 7/2005 |
| WO | WO 2006/005075 A2 | 1/2006 |
| WO | WO 2006/034125 A2 | 3/2006 |
| WO | WO 2006/059331 A2 | 6/2006 |
| WO | WO 2006/070367 A2 | 7/2006 |
| WO | WO 2006/103665 A2 | 10/2006 |
| WO | WO 2006/114649 A1 | 11/2006 |
| WO | WO 2007/028035 A3 | 3/2007 |
| WO | WO 2007/126246 A2 | 11/2007 |
| WO | WO 2007/126247 A1 | 11/2007 |
| WO | WO 2007/143200 A2 | 12/2007 |
| WO | WO 2007/149559 A2 | 12/2007 |
| WO | WO 2008/014432 A2 | 1/2008 |
| WO | WO 2008/016194 A2 | 2/2008 |
| WO | WO 2009/022343 A2 | 2/2009 |

* cited by examiner

Graph of acoustic power at focal point at constant radius, and Y=0

$FWHM_\theta = 0.646\text{deg}$ $FWHM_x = 0.118\text{mm}$ $\dfrac{FWHM_x}{\lambda} = 0.879$ Graph of acoustic power at focal point at constant radius, and θ=0

$FWHM_y = 0.305\text{mm}$ $\dfrac{FWHM_y}{\lambda} = 2.261$

Graph of acoustic power at focal point at constant radius, and Y=0

$FWHM_\theta = 0.664$ deg $FWHM_x = 0.075$ mm $\dfrac{FWHM_x}{\lambda} = 0.559$

Graph of acoustic power at focal point at constant radius, and θ=0

$FWHM_y = 0.08$ mm $\dfrac{FWHM_y}{\lambda} = 0.595$

Graph of acoustic power at focal point at constant radius, and Y=0

$FWHM_\theta = 0.653$ deg $FWHM_x = 0.177$ mm $\dfrac{FWHM_x}{\lambda} = 1.312$

Graph of acoustic power at focal point at constant radius, and θ=0

$FWHM_y = 0.596$ mm $\dfrac{FWHM_y}{\lambda} = 4.426$

ULTRASOUND SCANNING CAPSULE ENDOSCOPE (USCE)

CROSS-REFERENCE TO RELATED APPLICATIONS

The present application claims the benefit of U.S. Provisional Patent Application No. 61/318,012, filed on Mar. 26, 2010, entitled "Ultrasound Scanning Capsule Endoscope (USCE)," which is incorporated by reference herein in its entirety.

FIELD OF THE INVENTION

The present invention relates to ultrasound imaging on a capsule endoscope platform. It relates to the generation of a focused ultrasound acoustic signal and the receiving of echo signals from the wall of a body lumen with an array of acoustic transducers wrapped around the circumference of the capsule. It relates to sending the generated echo image signals to receiver devices attached or worn on the body. It relates to the generation of 360° overlapping sidewall ultrasound scans of a body lumen, and image processing techniques to assemble these scans into a high resolution continuous ultrasound image. Finally, it relates to the manufacture and assembly of such an ultrasound scanning capsule endoscope (USCE). The concept is extendable to conventional endoscopes and catheters.

BACKGROUND OF THE INVENTION

The population of the United States is aging. The first wave of the 78 million "Baby Boomers" is beginning to turn 60 years old. Coinciding with this aging of population is a rising concern regarding the public health, and a generally more educated patient in technology awareness. Some conditions, such as cancer, are most responsive to treatment if caught in the early stages. Cancer, for example, is best detected in the digestive tract. Given that cancerous growth can occur in as little as one to two years, it is essential to detect cancer or cancerous precursors at least annually, or preferably biannually. Physician and health care resources are currently already stretched and will fail if the current technology, process and procedure are not altered to suit the needs of the baby boomer market of the near future. Time-saving and simple solutions to diagnostics are needed.

The current population desires speedy testing and fast answers to their health questions. Many current testing and monitoring systems are limited by old technology and processes that takes days if not weeks for results. These test methods if not inconvenient and potentially embarrassing are at least in most cases intrinsically painful or risky to patients.

Thus, what is needed are diagnostic devices, services and processes that are simple, convenient, relatively inexpensive, comfortable, take less time, directly detect specific compounds or indicators to disease, and have more applications.

BRIEF DESCRIPTION OF THE DRAWINGS/FIGURES

The accompanying drawings illustrate the present invention and, together with the description, further serve to explain the principles of the invention and to enable one skilled in the pertinent art to make and use the invention.

DETAILED DESCRIPTION OF THE INVENTION

Introduction

Novel approaches to small bowel capsule endoscopy that uses an optical train to capture 360° overlapping sidewall scans of the small bowel, and image processing techniques to assemble these scans into a high resolution continuous image have been developed. This Optical Scanning Capsule Endoscope (OSCE) is a revolutionary step forward providing for 100% coverage of the intestinal tract including the small and large bowels. The image assembly techniques are not specific to optical images, which provide the opportunity to replace the optical imaging hardware with ultrasound imaging. An Ultrasound Scanning Capsule Endoscope (USCE) is envisioned which would use ultrasound imaging elements in an annular (ring-like) array around the circumference of the capsule to produce an image of reflected acoustic energy from the body lumen wall, and would use the same signal processing algorithms to assemble sequential ring scan frames into a single continuous image of the colon. Because the ultrasound signal would be reflected from the interface between the colonic contents and the colon tissue itself, it may not be necessary to prep the patient for this procedure. This sidewall ring scanning approach, when extended to ultrasound imaging rather than optical imaging, could enable prep-less imaging of the colon for Colorectal Cancer screening.

The OSCE technology platform effectively implements a 256 to 512 by 16 to 32 element wide optical scanning array around the circumference of a nominally 11 millimeter diameter capsule. It operates at up to 60 frames per second to accommodate rapid peristalsis movement (up to 5 cm per second) and tumbling. Optical flow algorithms, similar to those used in optical mice for computers, are used to track capsule movement. This movement information is used to vary the scan rate to minimize scan redundancy when stationary. Stitching algorithms, similar to those commercially available, are used to construct a single image of the entire intestine, which can be viewed and manipulated much like Google maps. The scan data is transmitted from the capsule to on-body sensors using the acoustic data communication technology described herein.

The USCE will be implemented by replacing the optical scanning array with an ultrasound scanning array. This scanning array swap will be built on top of the technology platform developed for the OSCE. The proposed USCE technical approach is described in detail below.

Key Design Considerations

Figure 1:
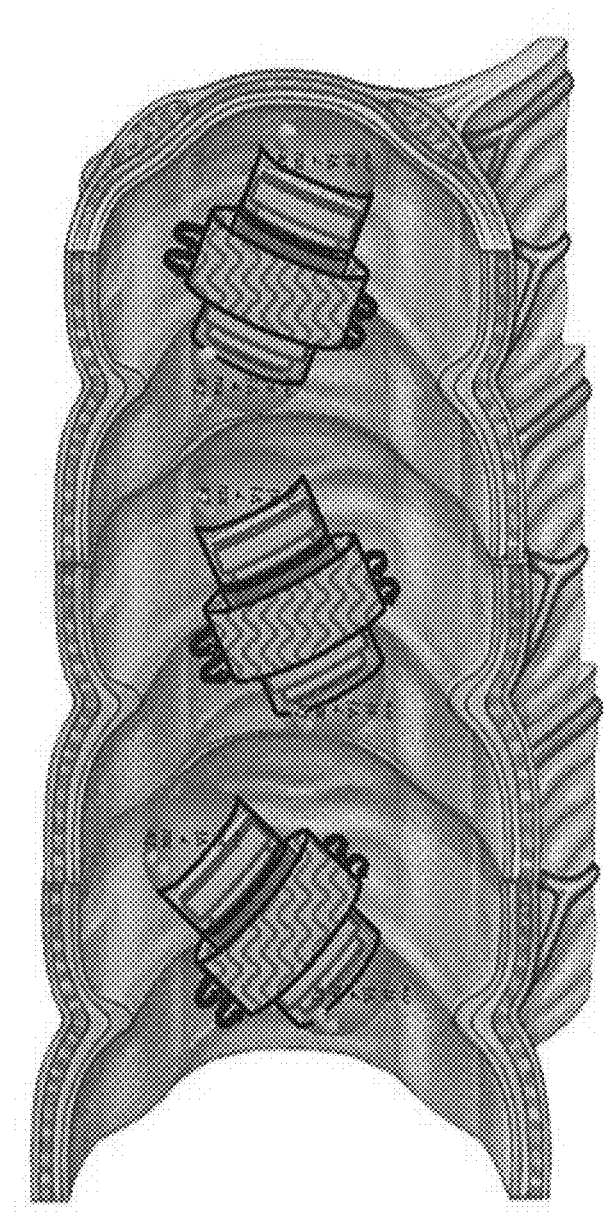
FIG. 1 is a drawing of the USCE in the intestinal tract.
Figure 2:
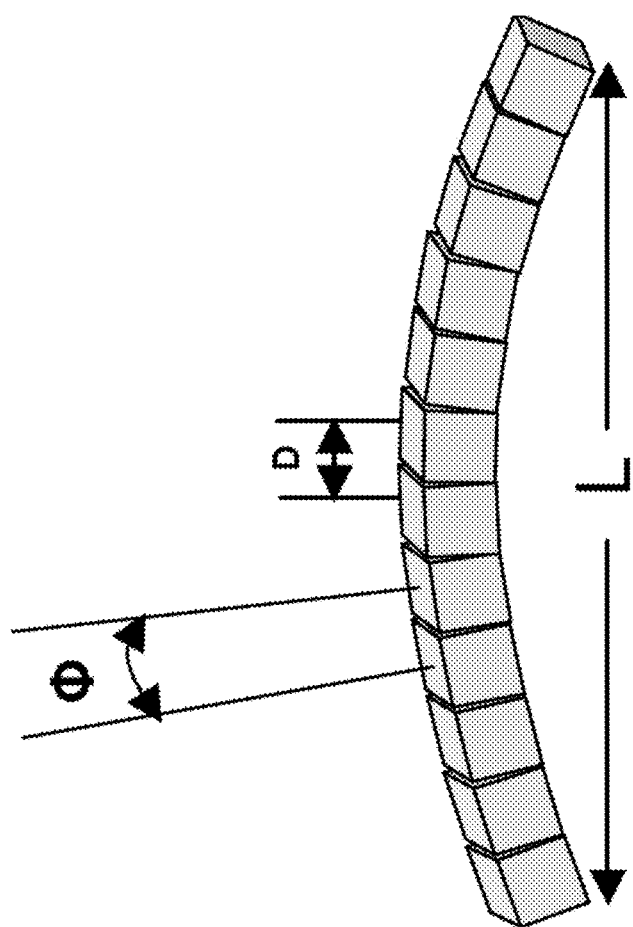
FIG. 2 is a drawing of the acoustic transducer array encircling the capsule endoscope.
Figure 3:
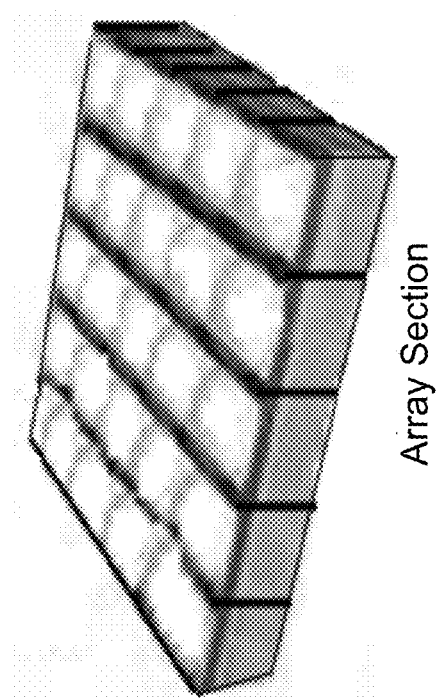
FIG. 3 shows the construction of a section of the transducer array.

There are several key design trade-offs that need to be considered to optimize the performance of the ultrasound scanner involving frequency of operation, acoustic element size and surface area, array size, transmit and receive power, battery current, and desired "image" voxel size, which is the spot size of the focused acoustic energy on the intestinal wall. FIG. 1 is an illustration of the USCE in the intestinal tract, showing how the focused acoustic energy impinges on the intestinal wall and is reflected back to the capsule. FIG. 2 illustrates the transducer array wrapped around the circumference of the capsule. The acoustic transducers could be implemented with PZT elements, but other technologies could also be employed. FIG. 3 shows a section of the array, illustrating its cross section. For the following discussion, the term "phased array" signifies the part of the total array that is energized for the generation of a focused acoustic signal at a spot on the intestinal wall.

The smallest spot size, $S_p$, defined as the diameter of the focused energy between first zeros, that acoustic energy may be focused to is given by:

$$S_p = 2\lambda l_f/L, \tag{1}$$

where L is the side dimension of the phased array, and $l_f$ is the focal length, given by the distance, d, from the array center to the intestinal wall. The wavelength of the sinusoidal acoustic signal is $\lambda = c/f$ where c=1540 meters/sec is the speed of sound in the aqueous environment of the intestinal track, and f is the signal frequency.

The depth of focus, $F_d$ is then given by:

$$F_d = S_p^2/(2\lambda). \tag{2}$$

For a given focal length, the spot size is determined by $\lambda$ and L, both of which have practical limits. The wavelength is limited by signal attenuation and L is limited by the curvature of the capsule. The term $l_f/L$ is the f-number which in practice is hard to get much smaller than unity, which limits the spot size to somewhat less than $2\lambda$, to no smaller than $\lambda$. The depth of focus increases as spot size increases, and some cases it may be desirable to increase the depth of focus at the expense of increased spot size, such as for when d is not well known. The optimization of $\lambda$ and L for array performance are next considered.

Figure 4:
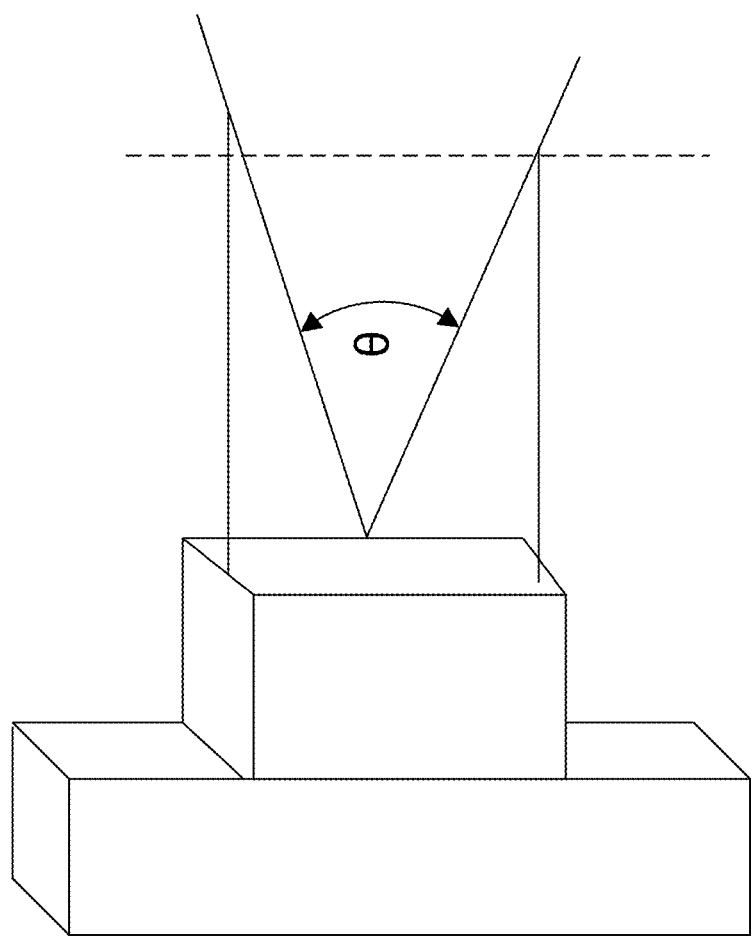
FIG. 4 illustrates the acoustic signal divergence angle from a single acoustic transducer element.

For optimal operation, the operational frequency needs to be chosen so that its wavelength, $\lambda$, is a multiple of the center-to-center transducer element spacing, D. Hence, $\lambda = mD$, where m=1 or 2 for this example implementation, although other values could be used and still fall under the scope of this invention. For a given D, m=1 would appear to provide for the smallest spot size from equation (1). But the focused array dimension, L, is constrained by the signal divergence angle, $\Theta$, from the acoustic transducer elements, as shown in FIG. 4 and given by:

$$\Theta = \sin^{-1}(K\lambda/D), \tag{3}$$

where K=0.433 for the half power point of the signal.

Figure 5:
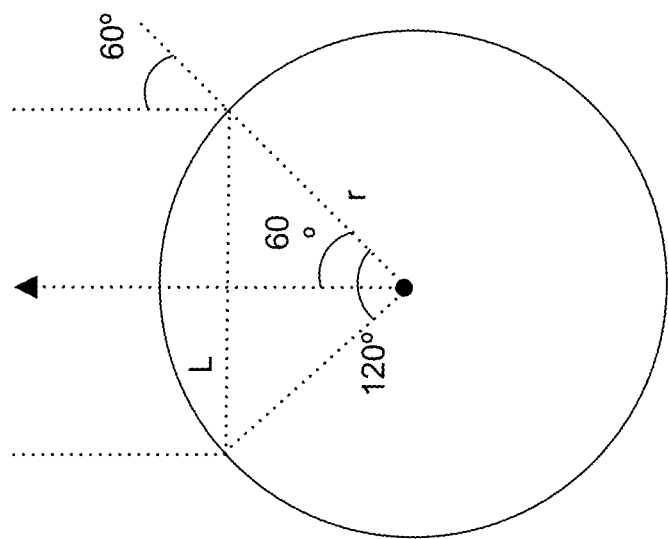
FIG. 5 shows the maximum phased array size around the capsule circumference.

For $\lambda = 2D$, the acoustic signal half power point occurs at $\Theta = 60°$. For $\lambda = D$, $\Theta = 26°$. The resulting difference in array size between these two angles is significant because of the surface curvature around the circumference of the capsule. Because of this curvature, the circumference transducer elements will have an angle between the elements, as shown on FIG. 2, given by:

$$\Theta = 360°/N \tag{4}$$

where N is the number of acoustic transducer elements around the circumference. The maximum array size for the circumference transducer elements is limited by the resultant curvature angle of the edge elements relative to the image spot. For $\lambda = 2D$, this will be the $\Theta = 60°$ divergence angle. The maximum focused array size is achieved in the limit of a very large imaging distance (going theoretically to infinity) between the intestinal wall and the center of the acoustic transducer element array where the array around the circumference would be a full third of the circumference (120°). However, the effective array aperture is the planar projection of this arc as shown in FIG. 5:

$$L_{max} 2r \sin(\Theta) = 2rK\lambda/D, \tag{5}$$

from equation (3) above, and
where r is the radius of curvature of the capsule. For $\Theta = 60°$ provided by $\lambda = 2D$, $L_{max2} = 4rK$. For $\Theta = 26°$ provided by $\lambda = D$, $L_{max1} = 2rK$, which is half the value of $L_{max2}$. Therefore, either case for $\lambda$ provides for the same spot size from equation (1) in the theoretical limit of infinite image distance. Using $L_{max}$ in equation (1) shows that for L near $L_{max}$ the spot size in the circumference direction increases linearly with d=lf:

$$S_{plimit} = \frac{Dl_f}{rK}. \tag{6}$$

The array size in the axial direction is also constrained by the divergence angle through the relation:

$$L_{axial} = 2l_f \tan(\Theta). \tag{7}$$

For $\Theta = 60°$, provided by $\lambda = 2D$, $L_{axial} = 3.5\ l_f$ for which the f-number=$l_f/L_{axial}$=0.29. The spot size in the axial direction is then:

$$S_{paxial} = \frac{4D}{3.5} = 1.15D. \tag{8}$$

Because the f-number is much less than one, this spot size is probably not practically achievable. For $\Theta = 26°$, provided by $\lambda = D$, $L_{axial} = l_f$ for which the f-number=1 and the spot size in the axial direction is:

$$S_{paxial} = 2D. \tag{9}$$

Figure 6:
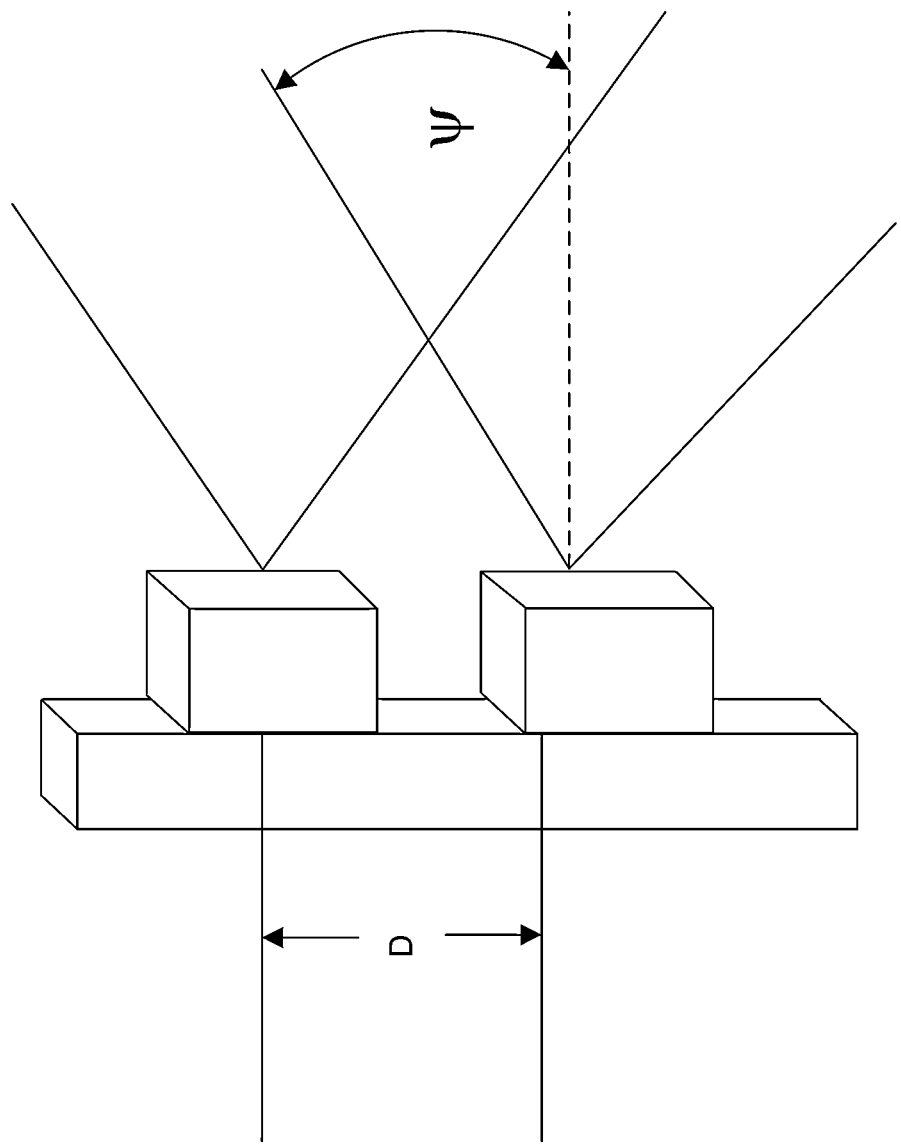
FIG. 6 illustrates the concept behind the array grating lobes.

Another key design consideration is the resulting signal pattern projected by the array. Of particular interest is what is termed the "grating" pattern, determined by:

$$\Psi_{gn} = \sin^{-1}(n\lambda/D) \tag{10}$$

where the center to center spacing of the transducer elements, D, is shown in FIG. 6 and n=n=±1, 2, 3, etc. for the grating lobes. The locations of the grating lobes are for the following parameters:

(a) λ=2D, $\Psi_{gn}$=N/A (no grating lobe)
(b) λ=D, $\Psi_{gn}$=±63°

For choice (a) above only the center beam is present with no grating lobes to confuse or complicate receiving an unambiguous ultrasound echo signal. Hence, the optimal design choice for the acoustic transducer array is λ=2D.

An example implementation is to implement N=512 transducer elements around a capsule diameter of 11 mm requiring a center-to-center spacing of D=67.5 microns for adjacent elements. A 10% overhead for spacing between elements gives a net transducer element size of 60 microns on a side, with 3.25 microns between elements. The wavelength is λ=2D=135 microns, which provides for a frequency of 11.4 MHz and a divergence angle of Θ=60°. Other design selections would fall under the scope of this invention. The maximum theoretical focused array size is considered to be one third of the circumference (2Θ=120°) for an arc length of 11.5 mm, which accommodates 170 elements. The planar projection is $L_{max}$=9.5 mm. The array dimension in the axial direction is given by $L_{axial}$=3.5 $l_f$. However, a practical focused array size may be smaller than this because of the tradeoff between spot size and operational complexity. Smaller arrays are simpler to implement, but the resulting spot size will be larger. Here, the practical array size will be limited to 32 transducer elements in the axial direction.

Scanner Operation

The phased array is set in the transmit configuration to launch a brief pulse focused to the minimum spot size at the targeted $l_f$ value, which could be the previously measured value for that voxel. The signal is focused by driving each element in the array with the appropriate timing so that the resulting wave front converges at the targeted spot. This is done with conventional approaches used in medical ultrasound imaging systems, except that the curvature of the array around the circumference needs to be accommodated in the signal timing to each element. Since the spot is not scanned, but is fixed to coincide with a point above the center of the array, the timing circuits are simplified by the array quadrant symmetry. So the number of timing circuits will be ¼ of the total number of transducer elements in the array. The timing circuits are further simplified by using one counter for the timer, with taps off the counter at the appropriate points for the correct timing of each transducer element in symmetric positions in all four quadrants. So four transducer elements are driven from each counter tap. The circuitry is further simplified by eliminating the 11.4 MHz oscillator circuit to drive the transducer elements for a short pulse, but by rather inducing resonant oscillation at 11.4 MHz with a brief impulse to the transducer elements. However, using an oscillator to drive the transducer elements would fall under the scope of the invention. The counter taps are programmable with algorithms that take the previous measurement data to set the appropriate timing taps for the next measurement.

Once the pulse has been launched, the array is configured into the receive mode, to listen for the signal echoes. In conventional medical ultrasound, the same phase array timing is used in the receive mode as for the pulse transmit mode. This approach is very complex, and requires a separate "front end" at each transducer element to detect a very weak return signal. However, because the transmit array provides a very well defined spot signal with no grating lobes, the receive array can be greatly simplified to just a small array of transducer elements at the center of the larger transmit array.

Medical ultrasound imaging receives multiple echo signals to re-construct a depth image of the object. Here, the USCE will be limited by the bandwidth of the communication channel to how much data can be acquired and sent.

The scanning operation is achieved by pulsing a single or multiple phased arrays configured around the circumference of the capsule. Once the echo signal is captured, a switching array configures the array elements for the next phased array, one element over around the circumference from the previous. In this way, one or multiple voxels around the array circumference are imaged at a time in sequence until all the circumference voxels have been imaged and the surface around the pill has been mapped. Then the process repeats using previously obtained data to set the arrays for the next data acquisitions. This process occurs very rapidly, resulting in a high net scan, or frame rate, whereby the capsule moves only a fraction of a voxel during peristalsis or tumbling, allowing for image stitching to capture a continuous, scanned image, as the capsule moves through the intestinal tract.

This scanning process measures a limited range of echo return times around expected echo times at the beam focus. The reflecting surface distance from the array is extracted from the dominant echo return time. This extracted surface distance is used as the focal distance for the next shifted voxel "probe". In this way the acoustic focus will closely follow the intestinal surface. An initial voxel scan will be need to gain the surface "lock", after which the scanning will be rapid.

Figure 7:
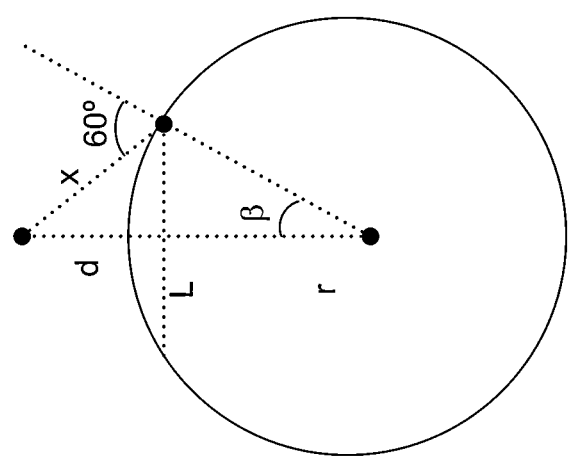
FIG. 7 shows the effective array aperture for the curved array for a particular focal distance.
Figure 8A:
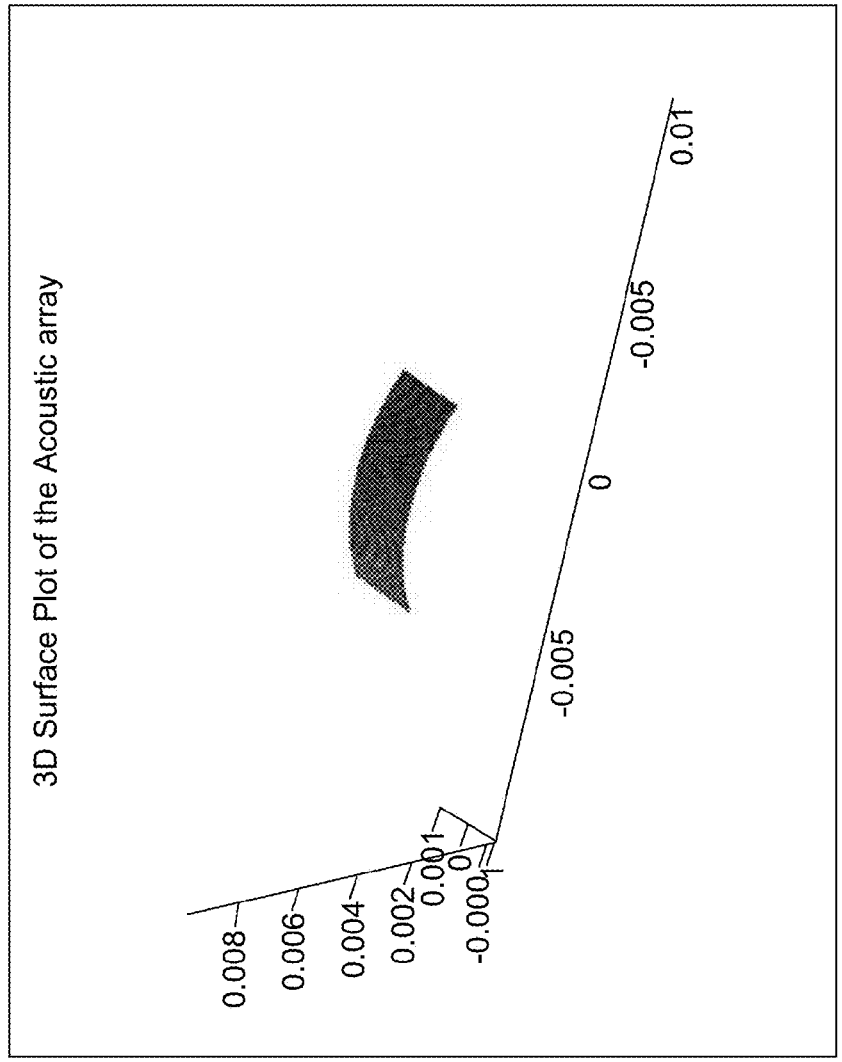
FIG. 8a shows a phased array configured to provide a focused acoustic beam for a simulation of the focused acoustic beam at a focal distance 5 mm away from the array surface.
Figure 8B:
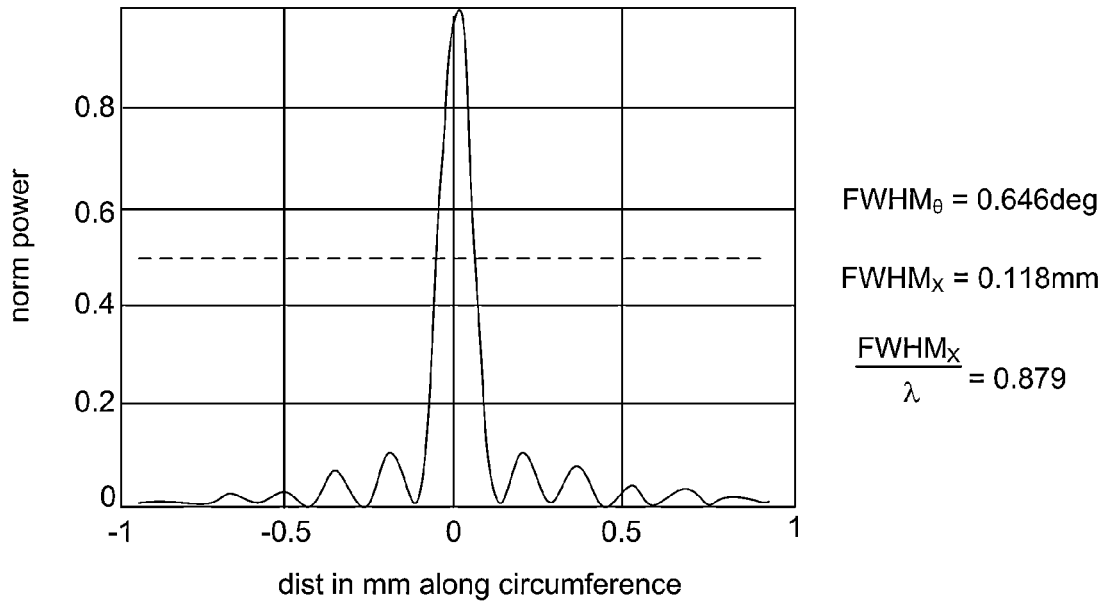
FIG. 8b is a graph of the resulting acoustic power at the focal point in the direction of the circumference and along the axial direction.
Figure 8B:
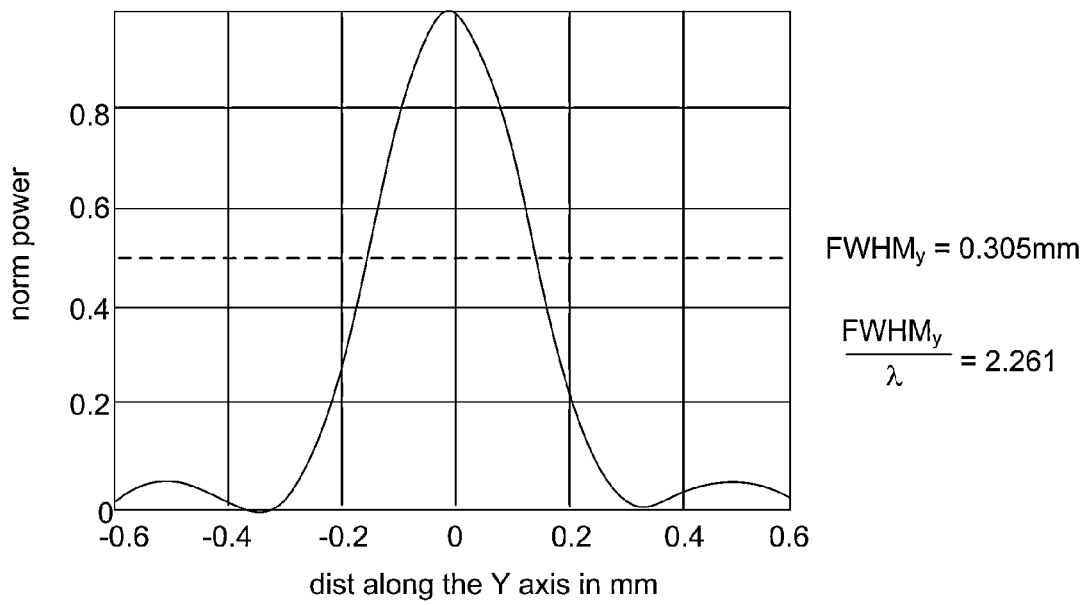
Figure 8C:
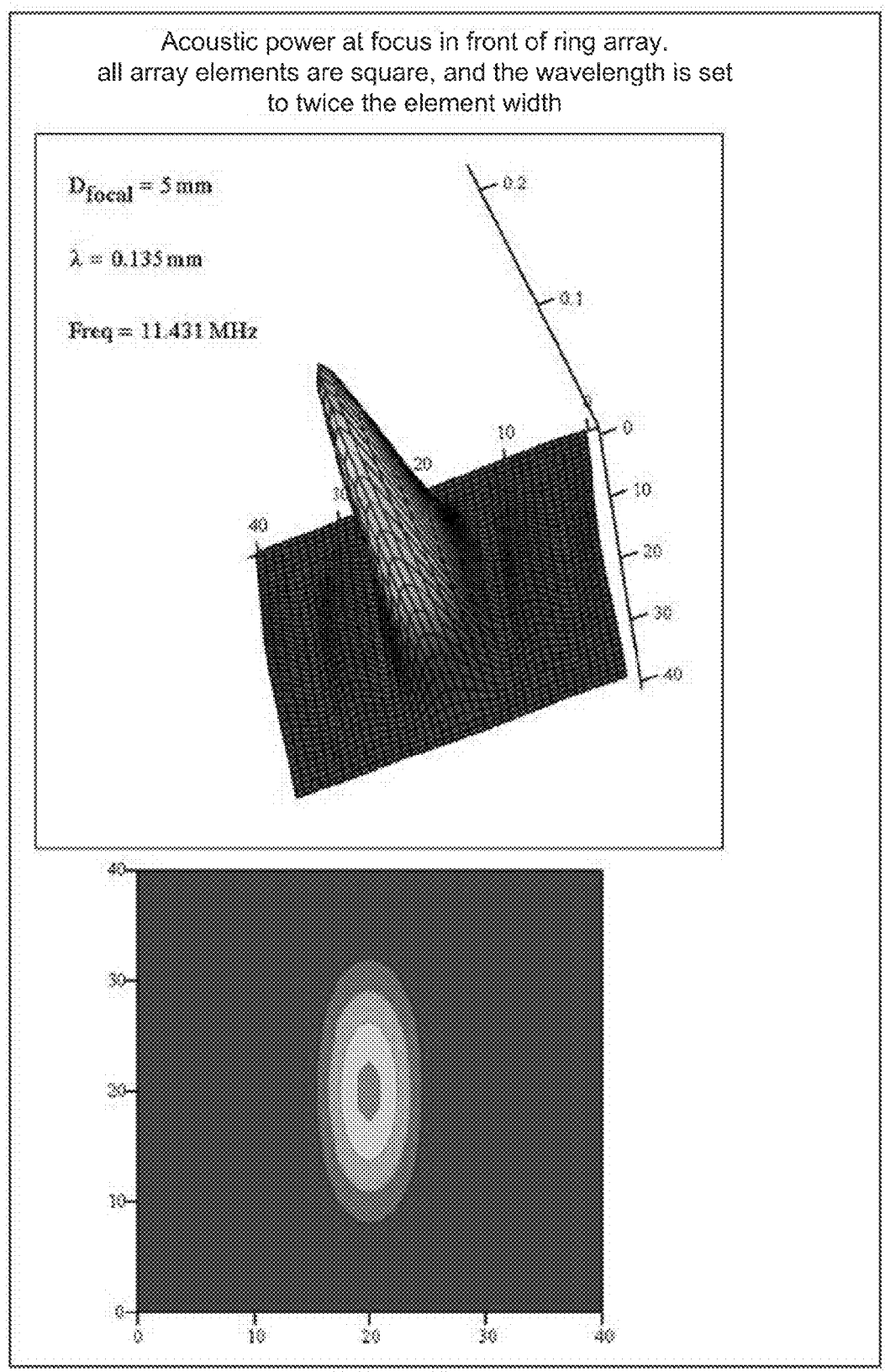
FIG. 8c is a three-dimensional presentation of the acoustic power, along with a top-down view.

An example of the above is provided for a distance of d=5 mm of the intestinal wall from the center of the transducer array. As discussed above, the array size, L, is limited by the curvature of the capsule, as shown in FIG. 7. The array size is given by:

$$L = 2r\sin(\beta), \text{ where from the law of cosines} \quad (11)$$

$$\beta = \tan^{-1}\left(\frac{.866}{.5 + \frac{r}{x}}\right), \text{ and} \quad (12)$$

$$x = -\frac{r}{2}\left[1 - \sqrt{1 + \frac{4d^2}{r^2}\left(1 + \frac{2r}{d}\right)}\right], \quad (13)$$

where r is the capsule radius. For d=5 mm, L=6 mm, and the selected phased array has 94 circumference transducer elements on a side. Using this value of L in equation (1) provides a theoretical spot size of 225 microns in the circumference direction, which provides the projected voxel size on the intestinal wall. The Mathcad simulation of FIGS. 8a-8c gives a circumference spot size of 242 microns between first zeroes. In the axial direction the number of transducer elements is 32, for an array dimension of 2 mm, which provides for a spot size of 625 microns. The Mathcad simulation gives an axial spot size of 654 microns between first zeroes. Therefore, the simulations confirm the theoretical predictions.

The number of such arrays, p, that can be "fired" at a time spaced equally around the capsule is in this case p=4. So four acoustic image voxels can be acquired in one transmit pulse period. Assuming a two wavelength acoustic pulse provides a total pulse period time of 0.175 usec. The maximum acoustic travel distance is from the array corners to the focused spot, given by:

$$d_{corner} = \sqrt{x^2 + \left(\frac{L_{axial}}{2}\right)^2}, \quad (14)$$

which for this example is 0.67 cm, providing for a round trip distance of 1.34 cm, which takes 8.7 usec. The total voxel acquisition time is therefore $t_a$=8.87 usec, which establishes the maximum voxel acquisition rate of:

$$R_{pixel} = \frac{p}{t_a}, \quad (15)$$

which for this case is 0.45 M voxels/sec. A complete scan of all the circumference voxels takes:

$$t_{scan} = \frac{Nt_a}{p} = \frac{N}{R_{pixel}}, \quad (16)$$

which for this case is 1.135 msec, providing for a scan rate of 881 scans/sec where each scan is comprised of 512 circumference voxels. During one scan the capsule moves 0.09 of a spot size in the axial direction at the maximum peristalsis rate of 2 inches/sec. The resulting voxel overlap between scans allows for image stitching to provide a continuous scanned image. Note that the above translates the array one transducer element center-to-center distance, or 67.5 microns, around the circumference for the next transmit pulse and echo receive cycle, which is 0.25 of the spot size for the circumference array. If the array is translated two transducer elements between cycles, or a 0.5 of a circumference spot size, then the scan rate doubles with the same data output rate, and the capsule then moves 0.045 of a spot size in the axial direction between scans, for greater voxel overlap, which enables post image processing that could increase effective resolution by at least a factor of two. Conversely, the scan rate can be kept the same to halve the data rate, which could be an important data bandwidth consideration.

The data channel will limit how many return echoes can be acquired and sent. If just one return echo were acquired, which would provide a topographical image of the intestinal wall, along with the echo signal strength, two digitized data values would have to be sent for each voxel. Assuming 8 bits per data value would yield a total of 16 bits/voxel times 0.45 Mvoxels/sec=7.2 Mbits/sec, which could be achieved by a variety of approaches and still fall under the scope of the invention. If data compression could be used, then for 10× data compression the channel would only have to provide for 0.72 Mbits/sec.

Prep-less colon applications will most likely require more echo data to resolve the signal traveling through non-homogeneous intestinal material. For this application, a higher data rate communication channel will need to be employed. Each echo time and signal strength data pair will require 7.2 Mbits/sec of bandwidth. Ten pairs would require 72 Mbits/sec, which with 10× data compression would require a 7.2 Mbit/sec channel. The actual number of data pairs required will most likely be less than ten, lessening the data rate requirements.

Figure 9A:
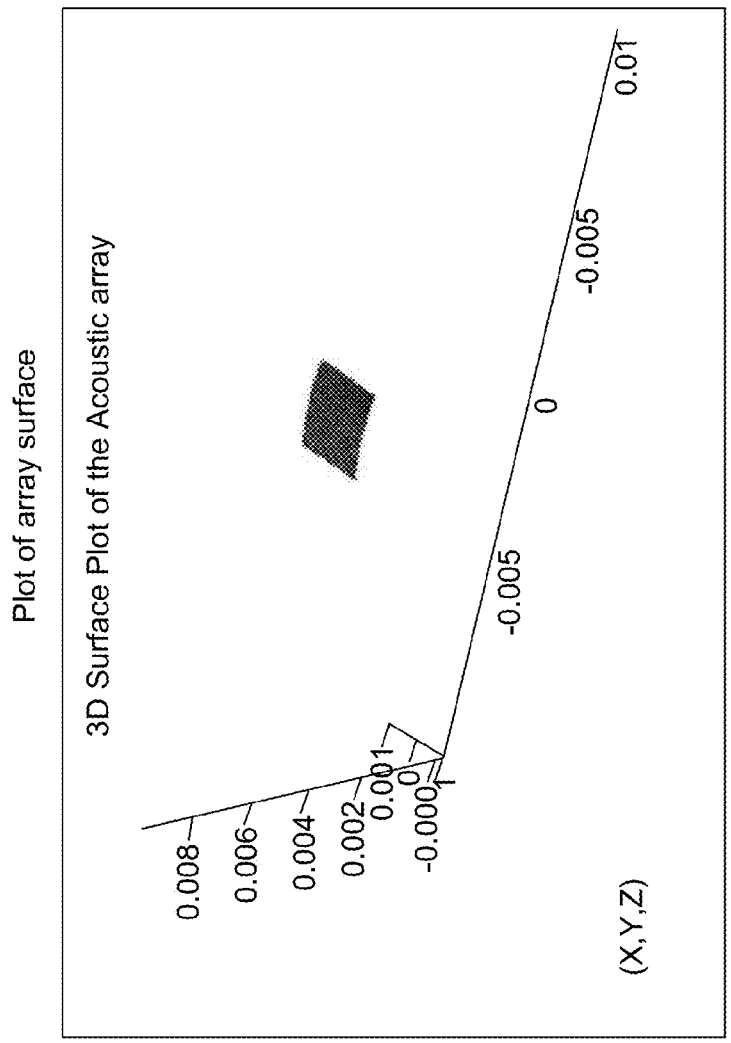
FIG. 9a shows a phased array configured to provide a focused acoustic beam for a simulation of the focused acoustic beam at a focal distance 1 mm away from the array surface.
Figure 9B:
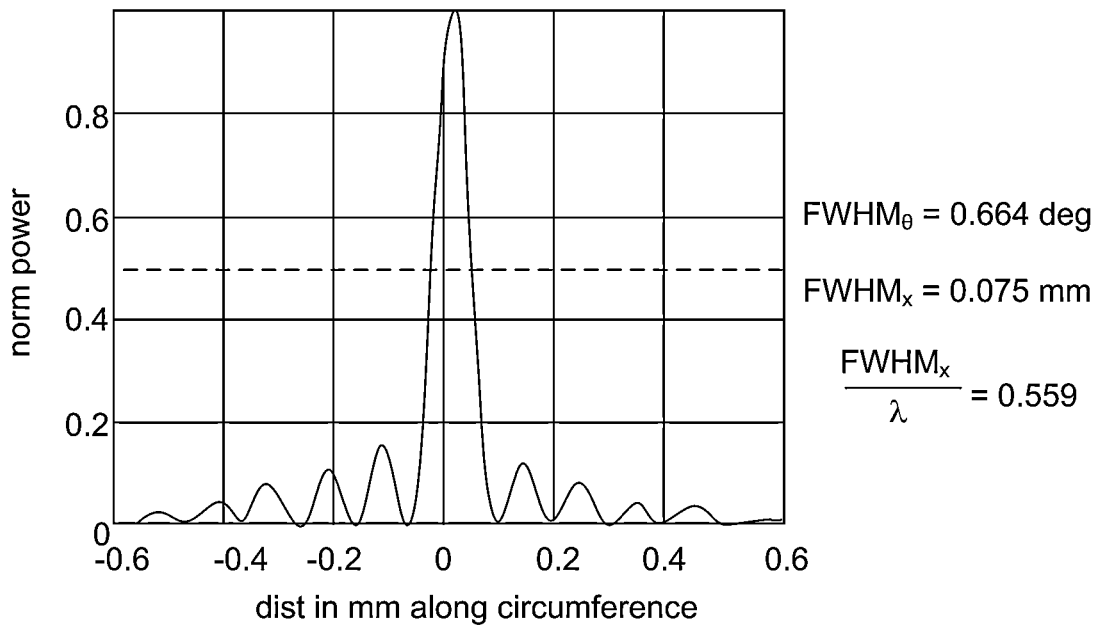
FIG. 9b is a graph of the resulting acoustic power at the focal point in the direction of the circumference and along the axial direction.
Figure 9B:
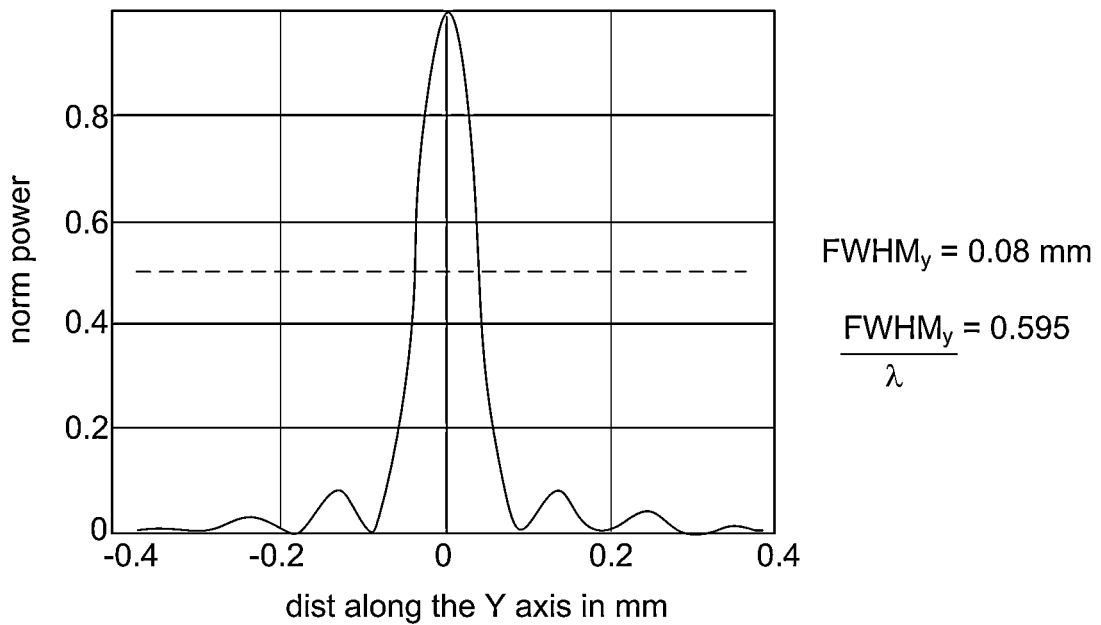
Figure 9C:
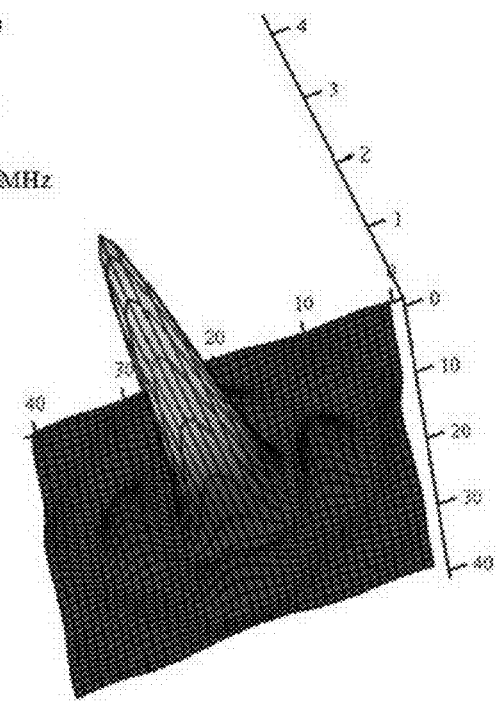
FIG. 9c is a three-dimensional presentation of the acoustic power, along with a top-down view.
Figure 9C:
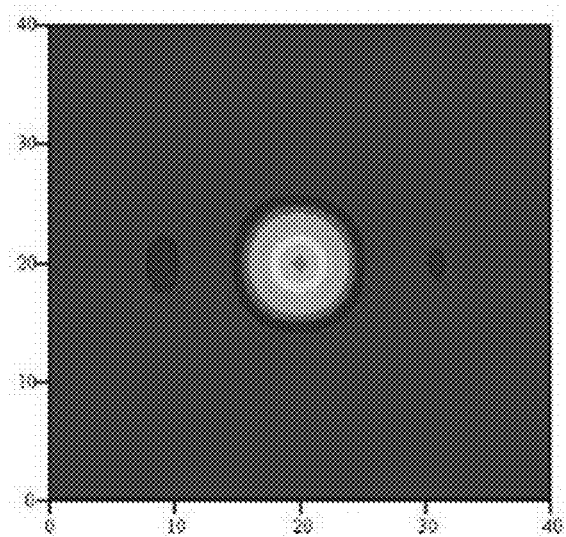

It is instructive to look also at calculations for when the intestinal wall is closer to the capsule. For a distance of d=$l_f$=1 mm of the intestinal wall from the transducer array, the array size is given by equation (11) to be L=2.45 mm comprising 36 transducer elements on a side. Using these values of L and $l_f$ in equation (1) provides an f-number of 0.4 and a theoretical spot size of 110 microns in the circumference direction. Because the f-number is much less than one, this spot size may not be realistically achievable. Indeed, the Mathcad simulation of FIGS. 9a-9c yields a spot size of 145 microns between first zeroes. In the axial direction the number of transducer elements is 32, for an array dimension of 2 mm, which provides for a spot size of 125 microns and an f-number of 0.46. Again, because the f-number is much less than one, this spot size may not be realistically achievable. Indeed, the Mathcad simulation of FIG. 9 yields a spot size of 170 microns.

Eight such arrays can be "fired" at a time equally spaced around the circumference of the capsule, for p=8. So eight acoustic image voxels can be acquired in one transmit pulse period. Repeating the calculations above for this yields $t_a$=2.76 usec, which establishes the maximum voxel acquisition rate of $R_{voxel}$=2.9 M voxels/sec and $t_{scan}$0.177 msec, providing for a scan rate of 5660 scans/sec where each scan is comprised of 512 circumference voxels. During one scan the capsule moves 0.08 of a spot size width in the axial direction at the maximum peristalsis rate of 2 inches/sec. This overlap between scans allows for image stitching to provide a continuous scanned image. As with the previous discussion, the array can be stepped by two transducer elements around the circumference to either increase the axial voxel overlap by a factor of two, or to reduce the scan rate, and, therefore, reduce the required data rate.

Figure 10A:
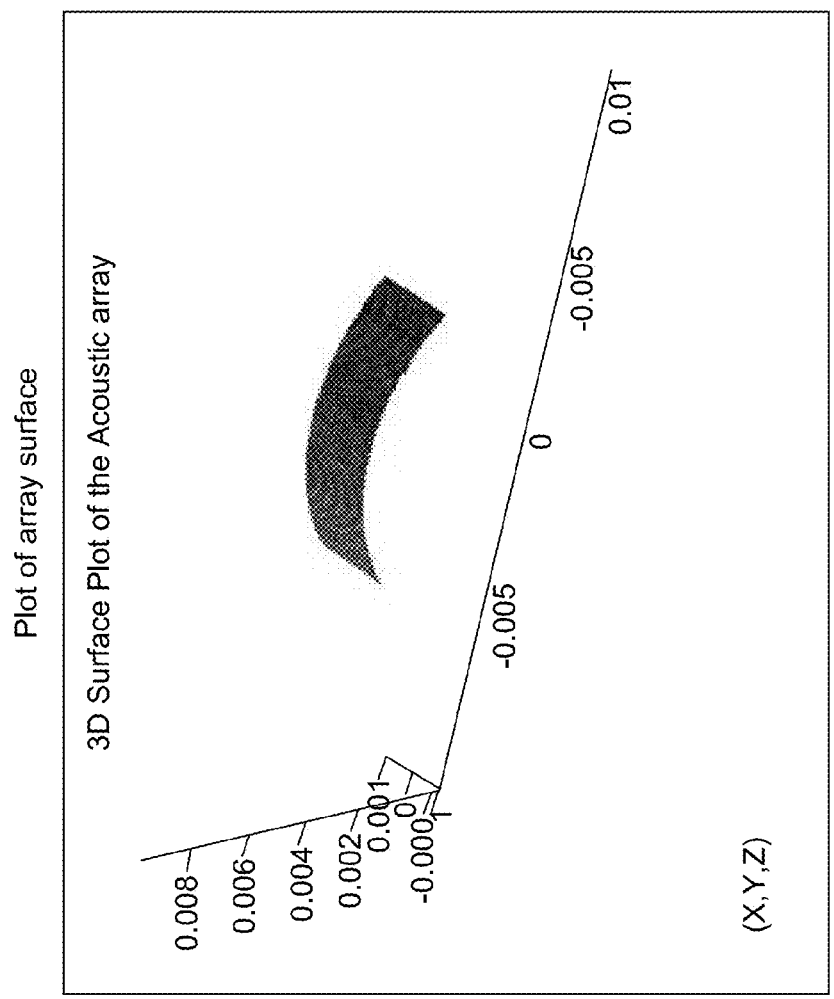
FIG. 10a shows a phased array configured to provide a focused acoustic beam for a simulation of the focused acoustic beam at a focal distance 10 mm away from the array surface.
Figure 10B:
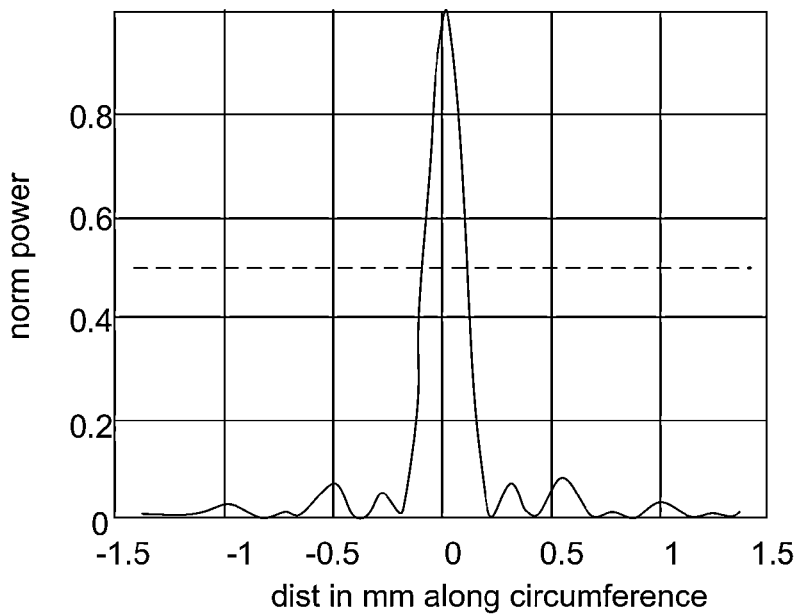
FIG. 10b is a graph of the resulting acoustic power at the focal point in the direction of the circumference and along the axial direction.
Figure 10B:
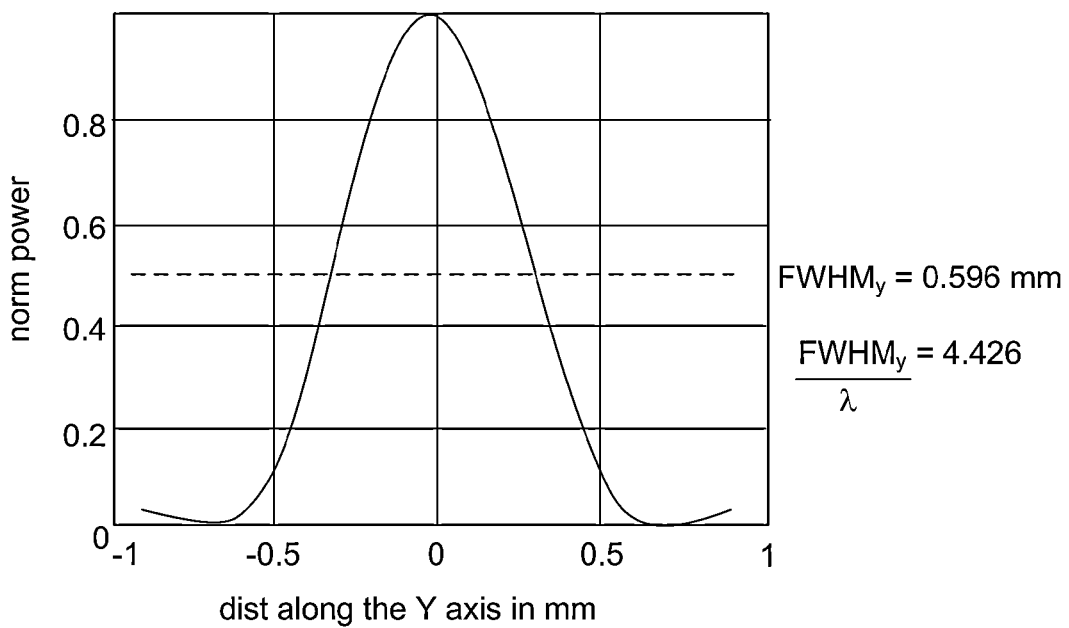
Figure 10C:
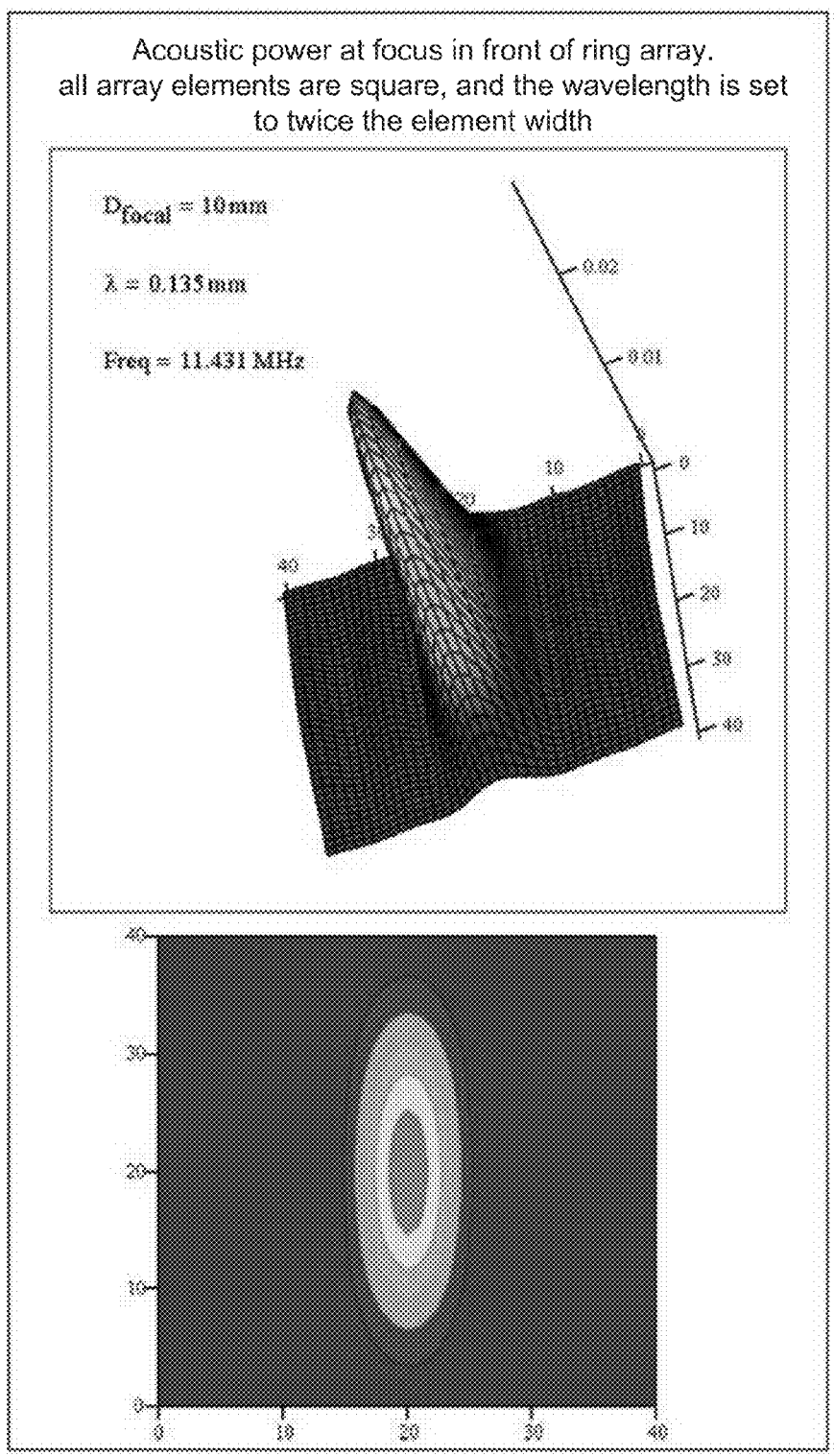
FIG. 10c is a three-dimensional presentation of the acoustic power, along with a top-down view.

Finally, it is useful to examine the case where the focused spot is further away, at d=1 cm. Now L=7.375 mm with 120 circumference elements and the spot size is 366 microns in the circumference direction. The axial spot size with 32 elements is 1250 microns. These results are confirmed by the Mathcad simulations of FIGS. 10a-10c, which gives a circumference spot size of 364 microns and an axial spot size of 1300 microns. Four such arrays can be "fired" at a time spaced equally around the capsule for p=4. So four acoustic image voxels can be acquired in one transmit pulse period. Repeating the calculations above for this yields $t_a$=15.8 usec, which establishes the maximum voxel acquisition rate of $R_{voxel}$=0.25 M voxels/sec and $t_{scan}$=2 msec, providing for a scan rate of 494 scans/sec where each scan is comprised of 512 circumference voxels. During one scan the capsule moves 0.08 of a spot size in the axial direction at the maximum peristalsis rate of 2 inches/sec. The resulting voxel overlap between scans allows for image stitching to provide a continuous scanned image. Note that the above translates the array one transducer element center-to-center distance, or 67.5 microns, around the circumference for the next transmit pulse and echo receive cycle, which is 0.3 of the spot size for the circumference array. If the array is translated two transducer elements between cycles, or a 0.6 of a circumference spot size, then the scan rate doubles with the same data output rate, and the capsule then moves 0.04 of a spot size in the axial direction between scans, for greater voxel overlap, which enables post image processing that could increase effective resolution by at least a factor of two. Conversely, the scan rate can be kept the same to halve the data rate, which could be an important data bandwidth consideration.

Timing Considerations

The timing of individual transducer elements in the array needs to be theoretically exact to provide for a converging acoustic signal wave front at the image point. For the acoustic signals from each transducer element to arrive at the focused spot simultaneously, the array elements are fired in order of their distance away from the array center, with the corner elements of the array firing first, and the center ones last. For the d=1 mm example above, the corner elements will need to be fired 0.644 usec before the center ones. The timing difference between adjacent transducer elements at and near the array edge is around 61 nsec. For elements closer to the center, the difference of acoustic travel distances becomes on the order of $0.5D^2/d$ between transducer elements, which for this case is 2.2 micron, or 1.5 nsec, which would require a clock frequency on the order of 670 MHz to drive a timing counter. The ratio of 0.644 usec/1.5 nsec is 429, which would require a 9-stage timing counter.

For the d=5 mm example above, the corner elements will need to fire 1.1 usec before the center ones. The timing difference between adjacent transducer elements at and near the array edge is around 114 nsec. For those at or near the center the timing difference between adjacent elements is about 0.3 nsec, which would require a clock frequency of 3.4 GHz to drive a timing counter. The ratio of 1.1 usec/0.3 nsec is 3367, requiring a 12-stage timing counter to accommodate.

An upper bound for the timing difference between corner elements and the center is for d becoming much larger than r, for which the array encompasses one third of the capsule circumference, and the difference in distance traveled to the focused spot becomes just ½ r. In this case ½ r,=2.75 mm, for an upper limit of 1.875 usec for when the corner elements need to fire before the center ones.

There is a difference in what is theoretically required for the timing of transducer array elements and what can be practically achieved. So it is necessary to examine how timing errors between tranducer elements affects array performance. Mathcad simulations were performed with phase shifted signals from the transducer elements to examine spot size vs array size, versus resolution of both phase and amplitude. The simulations showed excellent spot focus results for 1-bit resolution of the phase and 2-bits for the amplitude, as shown in FIGS. 8, 9 and 10. So two-bit resolution in the phase shift would then be more than adequate. This provides a $\lambda/4=33.75$ micron phase resolution, which is equivalent to a time resolution of about 22 nsec for a clock speed of 45 MHz. As discussed above, the maximum counter length is 1.875 usec, for a dynamic range of 1.875 usec/22 nsec=85, requiring a 7 stage counter. Other design selections would fall under the scope of this invention.

The transmit array counter will operate only when the transmit array is active. For the d=0.5 cm example above, the counter is active for 1.1 usec, and for d=0.1 cm, 0.64 usec. The total data acquisition times are 8.87 and 2.76 usec respectively, providing counter duty cycles of 12.4 and 23.2% respectively. As will be discussed in a later section, this same counter may also be employed as a timer for the receive signal.

Array Size Considerations

The focused array sizes around the circumference used in the above examples are limited by capsule curvature. As seen for the d=1 mm example, the resulting array provided an f-number of 0.4, which is less than is practically achievable. This provides for the possibility of reducing the array size to achieve an f-number that is more practically achievable. For example, an f-number=1 would be obtained with an array the size of $L=l_f$, yielding an array size of L=1 mm. More of this smaller array can be placed around the capsule, increasing scan rate. Also, the timing with the corner elements is faster, which further increases the scan rate. The disadvantage is that actual spot size will increase. This may be offset by the greater voxel overlap that increased scan rate with larger spot size will provide, allowing image processing techniques to recover enhanced resolution. Capsule curvature will limit the target achievability of $L=l_f$ as d increases. For d greater than 6.5 mm the array size will be limited by capsule curvature and the f-number will become greater than one.

As the capsule moves through the intestinal tract, it will be in positions where the distance, d, from the surface to the intestinal wall varies around the circumference. This situation will require dynamic array size configuration around the circumference as positions change. For example, d may vary from 1 mm on one side of the capsule to 5 mm on the other side. So as the array is stepped around the circumference as described above, the array size will vary to accommodate the changing value of d. The scan rate will also vary to accommodate the changing timing conditions of the array size. Stepping distance can also vary, as described above, to increase scan rate to maintain the desired amount of voxel overlap in the axial direction. This dynamic array environment will be directed by a central controller, which controls all aspects of array timing and size.

Receiver Issues

As discussed above, in a typical medical ultrasound scanner, once the timing is established for the transmit elements, the same timing is used for the receive elements to minimize image artifacts. Because of the complications of implementing that approach on a capsule platform, a simpler method is proposed, where only a block of transducer elements in the center of the array are is used as the receiver. To insure adequate phase coherence the block dimension is determined by the edge elements having a distance difference to the spot of no more than $\lambda/10$ than the center elements, which will ensure at least 95% constructive interference for the elements. For d=1 mm this constrains the block size to 311 microns on a side in the longitudinal direction, which accommodate 4.6 transducer elements, which is rounded down to 4. Around the circumference, the curvature also needs to be considered, and the array size is limited to 264 microns, which can accommodate 3.9 transducer elements, which is rounded up to 4. Therefore, the receive array contains a total of 16 transducer elements. The considerations for the number of receive array elements are by way of example only, and other considerations could yield a different number of receive array elements and still fall under the scope of the invention.

The receive array is configured as soon as the signal transmission cycle is completed and the signal oscillations are dampened. Upon the last transducer element transmission, which will be from the center-most elements, a clock timer is initiated, and the receive array starts listening for the echo signal from the intestinal wall tissue, distance d away from the array. The echo time will be that required for the acoustic signal to travel the round trip distance of 2d. For d=1 mm, this is 1.3 usec. If a distance resolution is desired equivalent to the depth of focus, 45 microns for this case, then the minimum timer increment would need to be 30 nsec, requiring the counter to be clocked at 34 MHz. A 6-stage counter would accommodate this count range. These range of numbers allow the same counter as used for the transmit array timing to be used for receive array timing. When the echo signal is detected, the counter downloads the count into a register for transmission to the external data receiver. Multiple echo detection would require a smaller time increment and a resultant higher clock rate for the counter.

Transmit and Receive Array Operation

The distance, d, of the focused spot on the intestinal wall to the array determines the optimal size and timing for both transmit and receive arrays. Since there is voxel overlap between scans, the previously measured value of d can be used to set up the array values for the next scan at the same location. This can be accomplished either through calculations or look up tables, or a combination of both. These values are then pre-loaded for immediate availability for the next scan. These array values would need to be stored in memory for each of the 512 voxel locations around the capsule circumference. For the d=1 mm case above, there are 36×32=288 transducer elements in each array quadrant, so 512×288=147,456 timing data points would need to be stored for the transmission arrays. An upper limit would be for large values of d where the effective array size is limited to one third the circumference of the capsule, which would have a total of 170×32=5,440 elements, for 1,360 in each quadrant. Than the number of timing points to be stored is 696,320.

For the first scan, there is no previously measured value of d, and capsule would go into "discover" mode for the first accurate measurement. One approach is to start with the minimum d value and step upward until an echo signal is received of the expected magnitude. This measured value of d would then be used for the next measurement at that location to hone in on and lock onto an accurate value.

The above discusses many design parameters that need to be optimized for the USCE. The choices for the design parameters selected above are by way of example only, and other choices would fall under the scope of the invention. Additionally, the concepts may be applied to formats other than a capsule, such as for endoscopes and catheters, for example.

Conclusion

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the present invention in any way.

What is claimed is:

1. An ultrasound scanning capsule endoscope, comprising:
a housing configured to have a size that is ingestible;
an ultrasonic transducer array wrapped around a circumference of the housing, each transducer in the ultrasonic transducer array being configured to transmit an ultrasonic signal and to receive an echo signal;
a timing circuit configured to induce transmission of a respective ultrasonic signal by each transducer according to a phased array sequence,
wherein the phased array sequence configures the ultrasonic transducer array into consecutive phased arrays around the circumference of the housing for sequentially imaging one or more voxels at a time around the circumference, and
wherein the consecutive phased arrays utilize a number of transducers when configured for transmission of their respective ultrasonic signals that is greater than a number of transducers when configured for reception of their respective echo signals.

2. The ultrasound scanning capsule endoscope of claim 1, wherein a wavelength of the ultrasonic signal transmitted by each transducer in the ultrasonic transducer array is related to a center-to-center transducer element spacing between adjacent transducers in the ultrasonic transducer array.

3. The ultrasound scanning capsule endoscope of claim 2, wherein the wavelength of the ultrasonic signal transmitted by each transducer in the ultrasonic transducer array is a multiple of the center-to-center transducer element spacing.

4. The ultrasound scanning capsule endoscope of claim 1, wherein each transducer in the ultrasonic transducer array is configured to enter into a receive mode of operation to listen for the echo signal after transmitting its respective ultrasonic signal in a transmit mode of operation.

5. The ultrasound scanning capsule endoscope of claim 1, wherein transducers in the ultrasonic transducer array that are further away from a center of their respective consecutive phased array provide their respective ultrasonic signals before transducers in the ultrasonic transducer array that are closer to the center.

6. The ultrasound scanning capsule endoscope of claim 1, wherein the consecutive phased arrays are configured and arranged to form a plurality of quadrants around the circumference, each of the plurality of quadrants being configured to simultaneously image one or more respective voxels from among the one or more voxels.

7. The ultrasound scanning capsule endoscope of claim 1, wherein the consecutive phased arrays are configured to sequentially image the one or more voxels around the circumference until all circumference voxels have been imaged.

8. The ultrasound scanning capsule endoscope of claim 1, wherein the consecutive phased arrays maintain a common center transducer when switching between transmission and reception configurations.

9. An ultrasound scanning capsule endoscope, comprising:
an ultrasonic transducer phased array wrapped around a circumference of a housing, each transducer in the ultrasonic transducer phased array being configured to transmit an ultrasonic signal and to receive an echo signal;
a timing circuit configured to induce transmission of a respective ultrasonic signal by each transducer in the ultrasonic transducer phased array according to a phased array sequence to sequentially image one or more voxels at a time around the circumference,
wherein each phased array within the phased array sequence utilizes a number of transducers when configured for transmission of its respective ultrasonic signal that is greater than a number of transducers when configured for reception of its respective echo signal.

10. The ultrasound scanning capsule endoscope of claim 9, wherein a wavelength of the ultrasonic signal transmitted by each transducer in the ultrasonic transducer phased array is related to a center-to-center transducer element spacing between adjacent transducers in the ultrasonic transducer phased array.

11. The ultrasound scanning capsule endoscope of claim 10, wherein the wavelength of the ultrasonic signal transmitted by each transducer in the ultrasonic transducer phased array is a multiple of the center-to-center transducer element spacing.

12. The ultrasound scanning capsule endoscope of claim 9, wherein each transducer in the ultrasonic transducer phased array is configured to enter into a receive mode of operation to listen for an echo signal after transmitting its respective ultrasonic signal in a transmit mode of operation.

13. The ultrasound scanning capsule endoscope of claim 9, wherein transducers in the ultrasonic transducer phased array that are further away from a center of their respective phased array provide their respective ultrasonic signals before transducers in the ultrasonic transducer phased array that are closer to the center.

14. The ultrasound scanning capsule endoscope of claim 9, wherein the ultrasonic transducer phased array is configured and arranged to form a plurality of quadrants around the circumference, each of the plurality of quadrants being configured to simultaneously image one or more respective voxels from among the one or more voxels.

15. The ultrasound scanning capsule endoscope of claim 9, wherein the ultrasonic transducer phased array is configured to sequentially image the one or more voxels around the circumference until all circumference voxels have been imaged.

16. The ultrasound scanning capsule endoscope of claim 9, wherein each phased array within the phased array sequence maintains a common center transducer when switching between transmission and reception configurations.

17. A method for imaging an intestinal tract, comprising:
  transmitting, by a first plurality of transducers, a first plurality of ultrasonic signals, each transducer from among the first plurality of transducers being part of a respective phased array from among a consecutive phased array that is wrapped around the circumference of an ultrasound scanning capsule;
  receiving, by a subset of the first plurality of transducers, a first plurality of echoes resulting from the first plurality of ultrasonic signals reflecting off of the intestinal tract to image one or more first voxels of the intestinal tract;
  transmitting, by a second plurality of transducers, a second plurality of ultrasonic signals each transducer from among the second plurality of transducers being part of another respective phased array from among the consecutive phased array; and
  receiving, by a subset of the second plurality of transducers, a second plurality of echoes resulting from the second plurality of ultrasonic signals reflecting off of the intestinal tract to image one or more second voxels of the intestinal tract.

18. The method of claim 17, further comprising:
  activating the second plurality of transducers after the first plurality of transducers have transmitted the first plurality of ultrasonic signals, the second plurality of transducers being closer to a center of their respective phased array than the first plurality of transducers.

19. The method of claim 17, further comprising:
  repeating the transmitting and the receiving steps for other plurality of transducers from among the consecutive phased array until all circumference voxels have been imaged.

20. The method of claim 17, wherein the step of receiving the second plurality of echoes comprises:
  receiving the second plurality of echoes to image the one or more second voxels that overlap the one or more first voxels.

21. The method of claim 17, wherein the step of transmitting the first plurality of ultrasonic signals comprises:
  transmitting the first plurality of ultrasonic signals having wavelengths that are related to a center-to-center transducer element spacing between adjacent transducers in their respective phased array.

22. The method of claim 21, wherein the step of transmitting the second plurality of ultrasonic signals comprises:
  transmitting the second plurality of ultrasonic signals having wavelengths that are related to a center-to-center transducer element spacing between adjacent transducers in their respective phased array.

\* \* \* \* \*